United States Patent [19]

Machida et al.

[11] Patent Number: 5,223,258

[45] Date of Patent: Jun. 29, 1993

[54] ANTIVIRAL DISINFECTING COMPOSITION AND METHOD OF INACTIVATING THE AIDS VIRUS IN VITRO

[75] Inventors: Makoto Machida, Tokorozawa; Makoto Yashiro, Tokyo; Kunichika Murakami, Iwakuni, all of Japan

[73] Assignee: Sanyo-Kokusaku Pulp Co., Ltd., Tokyo, Japan

[21] Appl. No.: 463,350

[22] Filed: Jan. 11, 1990

[30] Foreign Application Priority Data

Oct. 4, 1989 [JP] Japan ................................. 1-259347

[51] Int. Cl.$^5$ ..................... A01N 25/02; A61K 31/70; C08L 97/02
[52] U.S. Cl. .................................. 424/405; 424/400; 514/22; 514/885; 530/500; 530/507
[58] Field of Search ................. 424/400, 405; 514/22, 514/885; 162/11, 163; 530/500, 507

[56] References Cited

U.S. PATENT DOCUMENTS

| | | | |
|---|---|---|---|
| 4,191,610 | 3/1980 | Prior | 162/163 |
| 4,259,147 | 3/1981 | Gordy | 162/16 |
| 4,313,790 | 2/1982 | Pelton et al. | 162/163 |
| 5,110,414 | 5/1992 | Forss et al. | 162/163 |

OTHER PUBLICATIONS

Busnel et al., "Parameters of HIV inactivation by disinfectants", Int Conf. AIDS, Jun. 20–23, 1990, Abstract No. 1076.
Spire, Inactivation of lymphadenopathy associated virus by chemical disinfectants, Lancet, Oct. 20, 1984 (Abstract).
Goldberg et al., "The disinfectant potential of vinegar solutions used by Glasgow IDU's to prepare heroin for injection". Int Conf AIDS, Jun. 4–9, 1989 (abstract #Th.D.P.55).
Hanson et al., "Resistance of human immunodeficiency virus to disinfectants and fixatives", Int. Conf. AIDS, Jun. 4–9, 1989 (Abstract No. A.601).
Barre et al., "Inactivation of Lymphadenopathy associated virus (Lau) by Chemical and Physical Agents (meeting abstract), International Conference on Acquired Immunodeficiency Syndrome", Apr. 14–17, 1985, Atlanta, Ga. p. 69, 1985.
Resnick et al., "Stability and Inactivation of HTLV III/LAV under clinical & laboratory environments", JAMA, Apr. 11, 1986, 255(14) Abstract.
Montefiori et al., "Effective inactivation of human immunodeficiency virus with chlorhexidine antiseptics containing detergents and alcohol", J. Hosp. Infect., Apr. 1990, 15(3) Abstract.
Martin et al., "Inactivation of the HTLV-III/LAV virus", International Conference on Acquired Immunodeficiency Syndrome (AIDS), Apr. 14–17, 1985, Atlanta, Ga. p. 70, 1985 Abstract.
Chemical Abstracts, vol. 110, No. 23, p. 25, Jun. 5, 1989, H. Suzuki, et al., "Inhibition of the Infectivity and Cytopathic Effect of Human Immunodeficiency Virus by Water-Soluble Lignin in an Extract of the Culture Medium of Lentinus . . . ", 205157t.
Chemical Abstracts, vol. 97, No. 22, p. 387, Nov. 29, 1982, "Antiviral Lignin From Coniferous Trees"; 188266w.
Chemical Abstracts, vol. 92, No. 13, p. 78, Mar. 31, 1980, J. W. Ward, et al., "Combating Herpes Simplex Viruses With Lignosulfonates"; 404584j.
WPIL/Derwent Abstract, No. 90-070399, and JP-A-20-22231, Jan. 25, 1980.
Chemical Abstracts, vol. 112, No. 9, p. 34, Feb. 26, 1990, H. Suzuki, et al., "Lignosulfonate, A Water-Solubilized Lignin From the Waste Liquor of the Pulping Process, Inhibits the Infectivity and Cytopathic Effects of Human . . . "; 69555h.

Primary Examiner—Thurman K. Page
Assistant Examiner—Carlos Azpuru
Attorney, Agent, or Firm—Oblon, Spivak, McClelland, Maier & Neustadt

[57] ABSTRACT

An antiviral medicinal composition having spent liquor from kraft pulping and/or processed products thereof (kraft lignin, sulfomethylated and/or sulfopropylated kraft lignin) as major constituents, are effective agents in therapeutic and/or preventive methods against AIDS.

9 Claims, No Drawings

ANTIVIRAL DISINFECTING COMPOSITION AND METHOD OF INACTIVATING THE AIDS VIRUS IN VITRO

BACKGROUND OF THE INVENTION

The present invention contemplates to use spent liquor from kraft pulping and/or derivatives thereof as anti-AIDS agents for the prevention and therapy of infection by the AIDS virus.

So far, the only drug approved for therapeutic use against AIDS is azidothymidine (AZT). AZT is a nucleic acid-based derivative.

Moreover, drugs currently under development include compounds of dideoxy nucleic acid-based derivatives (e.g., dideoxycytidine, dideoxyadenosine, etc.), and sulfates of polysaccharides (e.g., dextran sulfate, etc.). However, they have problems in effectiveness from the points of toxicity, absorptivity, metabolism, etc. Thus, the development of other drugs exhibiting improved effectiveness is desired.

The present inventors have investigated the above problems diligently, and have previously applied for a patent concerning the antiviral action of spent liquor from pulping (Japanese Patent Application No. Hei 1-82691). Continued investigations have led to the discovery that, in particular, (1) spent liquor from kraft pulping (2) kraft lignin in the spent liquor from kraft pulping, and (3) sulfomethylated and sulfopropylated kraft lignins have excellent anti-AIDS activity. After confirming the effect against AIDS virus (HIV) (see Examples 1 to 4 infra), the present invention was completed.

SUMMARY OF THE INVENTION

The present invention provides an antiviral medicinal composition having spent liquor from kraft pulping, processed products thereof (kraft lignin, sulfomethylated and/or sulfopropylated kraft lignin), and mixtures thereof as major constituents. Furthermore, the present invention relates to therapeutic and/or preventive methods against AIDS using the same.

DETAILED DESCRIPTION OF THE INVENTION

The spent liquor from kraft pulping herein means the liquid portion obtained by separating pulp from the cooked material generated when wood is cooked with a liquor having sodium hydroxide and sodium sulfide as major ingredients.

As the woods to be used for this process, either hardwoods or softwoods are suitable. Mixtures of hardwood and softwood species are also suitable, and compositions having similar effects can be obtained using any wood.

The compositions of the invention can also be obtained by cooking herbs with a similar liquor.

Kraft lignin is also known as thiolignin. The product having the effects of the present invention can easily be obtained from the spent liquor from kraft pulping by any method known. Generally, methods of isolating kraft lignin, such as flocculation under heat after neutralization, acidic precipitation, fractionation with molecular sieves, or any combination thereof, are suitable for obtaining kraft lignin.

Sulfomethylated kraft lignin and sulfopropylated kraft lignin can be obtained, respectively, by sulfomethylating and sulfopropylating the kraft lignin isolated above. Any preparation method is suitable. However, the method of reacting under heat using sodium sulfite and formalin, and the method of reacting under heat using sodium sulfite and propanesultone are economically advantageous for sulfomethylation and sulfopropylation, respectively.

The articles of the present invention are expected to be used as preventive and therapeutic drugs against acquired immunodeficiency syndrome (AIDS) occurring in human beings as a result of infection by the AIDS virus (HIV), but they are particularly suitable for the prevention of infection.

Namely, effective inactivation and inhibition of propagation of the virus are achieved by using the articles of the present invention at the location of AIDS virus.

For instance, it is possible to accomplish the purpose of the present invention by containing the articles of the present invention in coat medicines, suppositories, ointments, tissue, etc., and by using them at the location of virus.

The recommended effective concentration is from about 0.5 to about 10,000 $\mu$g/g.

The articles of the present invention are low in toxicity against cells, and are clearly distinguished from general low-selectivity disinfectants.

In the following description, the present invention will be illustrated and exemplified in detail.

For the determination of the activity of AIDS virus, MT-4 cells were infected with HIV(LAV) for 1 hour at m,o,i=0.001 in the presence of each drug, and then cultured for 4 days. The amount of virus in the supernatant of the resulting medium was determined quantitatively according to the method of M. Asanaka et al (AIDS, 3 (1989), 403–404). The $ID_{50}$ value represents a concentration of the article of the present invention which inhibits infection by the virus by 50%.

EXAMPLE 1

The spent liquor from kraft pulping was neutralized to pH 10 with caustic soda, which was freeze-dried to obtain a powder.

The $ID_{50}$ of this product against the AIDS virus was 15 $\mu$g/ml. Moreover at 100 $\mu$g/ml toxicity against cells was not observed.

EXAMPLE 2

Using sulfuric acid, 100 ml of spent liquor from kraft pulping was adjusted to pH 3 to insolubilize kraft lignin. Then, the precipitated fraction was collected by centrifugal separation. The separated precipitate was washed with water, and converted to powder by drying under reduced pressure to obtain 4 g of a fraction having kraft lignin as a major ingredient.

Part of this product was suspended at a concentration of 1% in deionized water, and 1 N caustic soda was added thereto until the suspended matter dissolved. The solution was then freeze-dried to obtain a powder.

The $ID_{50}$ of the powder against the AIDS virus was 5 $\mu$g/ml. Furthermore, at a concentration of 100 $\mu$g/ml, toxicity against cells was not observed.

EXAMPLE 3

Ten g of a kraft lignin-rich fraction, obtained as in Example 2, was suspended in a concentration of 25%, and anhydrous sodium sulfite was added to this in an amount of 20% of the solids. Then, formaldehyde was added in an equimolar amount to the amount of sodium sulfite, and the mixture was allowed to react for 2 hours at 70° C., and then for 3 hours at 140° C. After cooling, dialysis was carried out using a dialyzing membrane for desalting, to obtain 8 g of sulfomethylated kraft lignin.

The $ID_{50}$ of the sulfomethylated kraft lignin against the AIDS virus was 3 μg/ml.

Moreover, at a concentration of 100 μg/ml, no toxicity was observed against cells.

EXAMPLE 4

A 1% solution of sulfomethylated kraft lignin was absorbed into tissue paper, resulting in a basis weight of 15 g/m$^2$ (1.5 wt.%, based on pulp), from which naturally-dried tissue was prepared.

Onto a 2 cm square section of this tissue paper, 10 μl of a liquor of AIDS virus was absorbed. After 5 minutes, the virus was collected by adding 10 ml of phosphate buffer saline.

In a separate procedure, the virus was treated similarly with a reference tissue not containing the sulfomethylated kraft lignin. Comparing the rate of killed virus, 99% or more of the virus was inactivated with the tissue containing the sulfomethylated kraft lignin of the present invention.

What is claimed is:

1. A method of inactivating AIDS virus in vitro, comprising treating a location exposed to the AIDS virus with a composition comprising a substance selected from the group consisting of kraft lignin, sulfomethylated kraft lignin, sulfopropylated kraft lignin or mixtures thereof, in an amount effective for the in vitro inactivation of the AIDS virus.

2. The method of claim 1, wherein said substance is absorbed into paper.

3. The method of claim 1, wherein said location is treated with said substance in a concentration of from 0.5 to 10,000 μg/g of said composition.

4. The method of claim 1, wherein said substance is kraft lignin.

5. The method of claim 1, wherein said substance is sulfomethylated kraft lignin.

6. The method of claim 1, wherein said substance is sulfopropylated kraft lignin.

7. The method of claim 2, wherein said substance is sulfopropylated kraft lignin.

8. The method of claim 5, wherein said sulfomethylated kraft lignin is prepared by reacting kraft lignin with sodium sulfite and formalin under heat.

9. The method of claim 6, wherein said sulfopropylated kraft lignin is prepared by reacting kraft lignin with sodium sulfate and propanesultone under heat.

* * * * *